(12) United States Patent
Kobayashi et al.

(10) Patent No.: US 7,906,651 B2
(45) Date of Patent: *Mar. 15, 2011

(54) METHOD FOR PRODUCING OPTICALLY ACTIVE HYDROXYMETHYLATED COMPOUNDS

(75) Inventors: Shu Kobayashi, Tokyo (JP); Kei Manabe, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 985 days.

This patent is subject to a terminal disclaimer.

(21) Appl. No.: 10/587,088

(22) PCT Filed: Jan. 27, 2005

(86) PCT No.: PCT/JP2005/001086
§ 371 (c)(1), (2), (4) Date: Jul. 21, 2006

(87) PCT Pub. No.: WO2005/073156
PCT Pub. Date: Aug. 11, 2005

(65) Prior Publication Data
US 2008/0269496 A1    Oct. 30, 2008

(30) Foreign Application Priority Data

Jan. 30, 2004 (JP) ................................. 2004-023338

(51) Int. Cl.
C07D 213/22 (2006.01)
C07C 47/00 (2006.01)
C07C 45/00 (2006.01)

(52) U.S. Cl. ......... 546/257; 546/260; 568/446; 568/449

(58) Field of Classification Search .................. 546/255; 568/446, 449
See application file for complete search history.

(56) References Cited

U.S. PATENT DOCUMENTS 7,541,307 B2 * 6/2009 Kobayashi et al. ........... 502/167
2008/0139835 A1    6/2008 Kobayashi et al.

FOREIGN PATENT DOCUMENTS

| JP | 06-166652 A | 6/1994 |
| JP | 6-256248 | 9/1994 |
| JP | 2001-252570 A | 9/2001 |
| JP | 2002-200428 | 7/2002 |
| WO | WO2005/073156 | 8/2005 |
| WO | WO2006/080425 | 8/2006 |

OTHER PUBLICATIONS

Denmark et al JACS 2002, 124, 4233-4235.*
http://medical-dictionary.thefreedictionary.com/aryl.*
Ishikawa et al Journal of the American Chemical Society 2004, 126, 12236-12237.*
Schneider et al Angewandte Chemie Internation Ed 2004, 43, 5691-5694.*
Ng et al Inorganic Chemistry Communications 2005, 8, 769-772.*
Denmark et al., "Catalytic, Enantioselective Aldol Additions to Ketones", JACS 2002, 124, 4233-4235.
Bolm et al., "Enantioselective Synthesis of Optically Active Pyridine Derivatives . .", Chem. Ber. 1992, 125, 1169-1190.
Manabe et al., "Lewis acid-catalyzed asymmetric hydroxymethylation of silicon enolates in aqueous media", Tetrahedron 59 (2003) 10439-10444.
Ozasa et al., "Aldol synthesis with an aqueous solution of formalin", Synlett 2003, pp. 2219-2221.
Ishikawa et al., "Catalytic Assymmetric Hydroxymethylation of Silicon Enolates . . . Chiral Scandium Complex", JACS 2004, 12236-12237.
Kobayashi et al., "Lanthanide Triflates as Water-Tolerant Lewis Acids", J. Org. Chem. 1994, 3590-3596.
Bolm et al., "Optish active bipyridine in der assummetriscen katalyse", Angew. Chem. 102 (1990), 206-208.
Casas et al., "Direct organocatalytic asymmetric α-hydroxymethylation of ketones and aldehydes," Tetrahedron Letters. No. 45 pp. 6117-6119 (2004).
European Supplementary Search Report corresponding to European Patent Application No. 06712459.4-1211 dated Feb. 4, 2009.
International Preliminary Report on Patentability corresponding to International Application No. PCT/JP2005/001086 dated Mar. 29, 2006.
International Preliminary Report on Patentability corresponding to International Application No. PCT/JP2006/301293 dated Jul. 31, 2007.
International Search Report corresponding to International Application No. PCT/JP2005/001086 dated Apr. 26, 2005.
International Search Report corresponding to International Application No. PCT/JP2006/301293 dated Jun. 6, 2006.
Kaku et al., "A Novel Route for Chiral Synthesis of the Triazole Antifungal ER-30346," Chemical and Pharmaceutical Bulletin. vol. 46, No. 7 pp. 1125-1129 (1998).

(Continued)

*Primary Examiner* — Rita J Desai
*Assistant Examiner* — John Mabry
(74) *Attorney, Agent, or Firm* — Jenkins, Wilson, Taylor & Hunt, P.A.

(57) ABSTRACT

The present invention presents a catalyst that allows asymmetric hydroxymethylation reactions to progress with excellent asymmetric selectivity and a production method for optically active hydroxymethylated compounds using the catalyst. Optically active hydroxymethylated compounds are obtained with excellent asymmetric selectivity by using a catalyst obtained by mixing chiral ligands (for example, chemical formula 4)

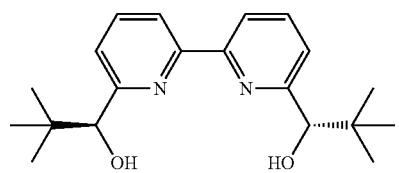

with scandium triflate and the like.

2 Claims, 1 Drawing Sheet

OTHER PUBLICATIONS

Kobayashi et al., "Bismuth Triflate-Chiral Bipyridine Complexes as Water-Compatible Chiral Lewis Acids," Organic Letters. vol. 7, No. 21 pp. 4729-4731 (2005).

Kobayashi, "Lanthanide Trifluoromethanesulfonates as Stable Lewis Acids in Aqueous Media. $Yb(OTf)_3$ Catalyzed Hydroxymethylation Reaction of Silyl Enol Ethers with Commercial Formaldehyde Solution," Chemistry Letters. pp. 2187-2190 (1991).

Kumar et al., "Lipase-Catalyzed Chemo- and Enantioselective Acetylation of 2-Alkyl/aryl-3-hydroxypropriophenones," Bioorganic & Medicinal Chemistry. vol. 9 pp. 2643-2652 (2001).

Kuwano et al., "Asymmetric aldol reaction of 2-cyanopropionates catalysed by trans-chelating chiral diphosphine ligand TRAP-rhodium(I) complex," Chemical Communications. pp. 71-72 (1998).

Notice of Allowance corresponding to U.S. Appl. No. 11/795,525, dated Mar. 20, 2009.

Official Action corresponding to U.S. Appl. No. 11/795,525, dated Nov. 26, 2008.

Reynolds et al., "The Intramolecular Carboxyarylation Approach to Podophyllotoxin," Journal of the American Chemical Society. vol. 125 pp. 12108-12109 (2003).

Wada et al., "Asymmetric trimethylsilylcyanation of aldehydes utilizing chiral bismuth compounds. A frontier in bismuth mediated synthetic reactions," Tetrahedron. vol. 8, No. 23 pp. 3939-3946 (1997).

Wadamoto et al., "Aldol Synthesis with an Aqueous Solution of Formalin," Synlett. No. 14 pp. 2219-2221 (2003).

Written Opinion of the International Searching Authority corresponding to International Application No. PCT/JP2006/301293 dated Jun. 6, 2006.

Wu et al., "Chemical studies on the chiral indanone derivatives as the inhibitor of *Renilla* luciferase," Tetrahedron. vol. 57 pp. 9575-9583 (2001).

\* cited by examiner

METHOD FOR PRODUCING OPTICALLY ACTIVE HYDROXYMETHYLATED COMPOUNDS

FIELD OF THE INVENTION

The present invention relates to an asymmetric hydroxymethylation reaction and more particularly to a production method for an optically active hydroxymethylated compound and an catalyst thereof.

PRIOR ART

The reaction between a silicon enolate and formaldehyde under the presence of a Lewis acid is a useful method to synthesize α-hydroxymethyl carbonyl compounds. However, a catalytic asymmetric reaction is extremely difficult to achieve, and examples with high selectivity have not been reported (References 1 to 5).

Reference 1:
Manabe, K.; Ishikawa, S.; Hamada, T.; Kobayashi, S. Tetrahedron 2003, 59, 10439.

Reference 2:
Ozasa, N.; Wadamoto, M.; Ishihara, K.; Yamamoto, H. Synlett 2003, 2219.

Reference 3:
Kuwano, R. et. al., Chem. Commun. 1998, 71.

Reference 4:
Casas, J. et. al., Tetrahedron Lett. 2004, 45, 6117.

Reference 5:
Bolm, C.; Ewald, M.; Felder, M.; Schlingloff, G. Chem. Ber. 1992, 125, 1169.

PROBLEMS TO BE SOLVED BY THE INVENTION

The present invention presents a catalyst that allows an asymmetric hydroxymethylation reaction to proceed with excellent asymmetric selectivity and a production method for optically active hydroxymethylated compounds using the catalyst.

MEANS TO SOLVE THE PROBLEMS

The inventors discovered that a catalytic asymmetrical hydroxymethylation reaction proceeded with excellent stereoselectivity when a combination of chiral ligands (see Reference 3) and a scandium triflate was used. The present invention was completed based on the discovery. A commercially available aqueous formaldehyde solution (formalin) can be used directly to the reaction.

The catalytic system of the present invention is not only useful in the synthesis of optically active materials but also can provide an important direction for the development of catalytic asymmetric reactions in aqueous media.

That is, the present invention is a method for producing an optically active hydroxymethylated compound, comprising reacting a silicon enolate and formaldehyde, in the presence of a catalyst, in an aqueous solution or a mixed solvent of water and an organic solvent, wherein the silicon enolate is represented by the following formula (chemical formula 2):

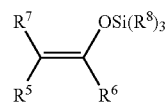

wherein $R^5$ to $R^7$ are hydrogen atoms, aliphatic hydrocarbon groups, monocyclic or polycyclic alicyclic hydrocarbon groups, monocyclic or polycyclic aromatic hydrocarbon groups or heterocyclic groups where $R^6$ is not a hydrogen atom, $R^5$ and $R^7$ are not identical, $R^5$ and $R^6$ may together form a ring and $R^8$, may be identical or different, are hydrocarbon groups, and the catalyst is obtained by mixing a ligand or its symmetric isomer and a Lewis acid, wherein the ligand is represented by the following formula (chemical formula 1):

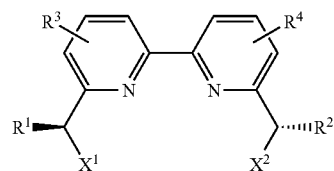

wherein $R^1$ and $R^2$, may be identical or different, are hydrogen atoms, alkyl groups or aryl groups, at least one of $R^1$ and $R^2$ contains at least three carbon atoms, $R^3$ and $R^4$, may be identical or different, are hydrogen atoms, alkyl groups containing one to four carbon atoms or alkoxy groups, $X^1$ and $X^2$, may be identical or different, are represented by —$OR^9$, —$SR^{10}$ or —$NHR^{11}$, wherein $R^9$ to $R^{11}$ are hydrogen atoms or alkyl groups, and the Lewis acid is represented by $MY_n$, wherein M is Cu, Zn, Fe, Sc or a lanthanoid element, Y is a halogen atom, OAc, $OCOCF_3$, $ClO_4$, $SbF_6$, $PF_6$ or $OSO_2CF_3$ and n is 2 or 3.

DETAILED DESCRIPTION OF THE INVENTION

Figure 1:
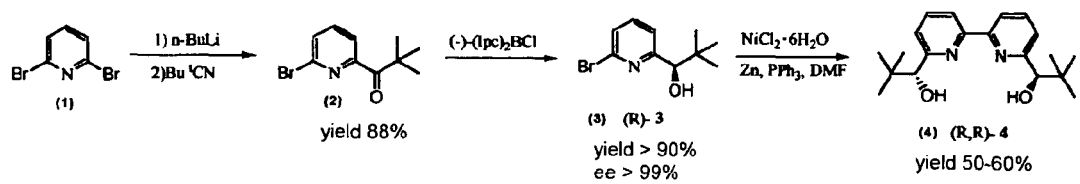
FIG. 1 shows a synthetic route for Ligand 1.

The catalyst used in the present invention is obtained by mixing a ligand having the following structure (chemical formula 1):

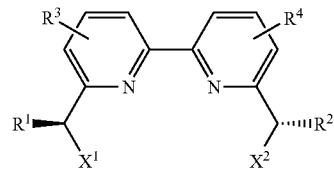

and a Lewis acid represented by $MY_n$.

$R^1$ and $R^2$ represent hydrogen atoms, alkyl groups or aryl groups, preferably alkyl groups or aryl groups. They may be identical or different, preferably identical. At least one of $R^1$ and $R^2$ needs to be bulky and, more specifically, needs to contain at least three carbon atoms.

$R^3$ and $R^4$ represent hydrogen atoms or alkyl or alkoxy groups having one to four carbon atoms but are preferably hydrogen atoms. They may be identical or different, preferably identical.

$X^1$ and $X^2$ represent —$OR^9$, —$SR^{10}$ or —$NHR^{11}$, preferably —OH or —OMe, where $R^9$ to $R^{11}$ represent hydrogen atoms or alkyl groups with hydrogen atoms preferred, and the number of carbon atoms in the alkyl groups is 1 to 3.

M represents Cu (divalent), Zn (divalent), Fe(divalent or trivalent), Sc (trivalent) or lanthanoid elements ($^{57}$La to $^{71}$Lu) (trivalent) but preferably represents Sc.

n represents an integer corresponding to the valence of M and represents 2 or 3.

Y represents a halogen atom, OAc, $OCOCF_3$, $ClO_4$, $SbF_6$, $PF_6$ or $OSO_2CF_3$(OTf), preferably OTf.

When this ligand and a Lewis acid represented by $MY_n$ are mixed in a solvent, a catalyst is formed by coordinating M in the ligand. $H_2O$-DME, $H_2O$—$CH_3CN$, $H_2O$-THF, $H_2O$-1,4-dioxane, $H_2O$-EtOH, $H_2O$-MeOH, $H_2O$—PrOH, water and the like may be cited as the solvent used. Each concentrations in the solvent is preferably from about 0.01 mole/liter to about 0.1 mole/liter.

In the present invention, this catalyst is used in asymmetric hydroxymethylation reactions of formaldehyde and a silicon enolate as described below (chemical formula 3):

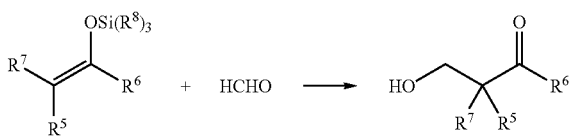

$R^5$ to $R^7$ represent hydrogen atoms, aliphatic hydrocarbon groups, monocyclic or polycyclic alicyclic hydrocarbon groups, monocyclic or polycyclic aromatic hydrocarbon groups or heterocyclic groups. However, $R^6$ is not a hydrogen atom, and $R^5$ and $R^7$ are not the same. In addition $R^5$ and $R^6$ may together form a ring and they may also contain substituents. As this hydrocarbon group or the heterocyclic group, alkyl groups such as methyl, ethyl, propyl, isopropyl, butyl and the like, cyclohexyl groups, phenyl groups, benzyl groups, phenyl ethyl groups, phenyl vinyl groups, naphthyl groups, furyl groups, thienyl groups, silyloxy groups and the like may be listed as examples. In addition, a variety of substituents such as halogen atoms, alkoxy groups, thio ether groups, hydrocarbon groups and the like may be listed as substituents that may be attached to these.

$R^5$ to $R^7$ are preferably as described below:

$R^5$ represents a hydrogen atom or an alkyl group, and $R^6$ represents an alkyl group, an alkyl aryl group, an aryl group or a sulfide group. However, $R^5$ and $R^6$ may together form a ring, the ring may optionally contain a hetero atom or a portion of an aromatic ring and the ring is preferably a five to seven membered ring comprising a hydrocarbon. $R^7$ represents a hydrogen atom, an alkyl group, an alkyl aryl group, an aryl group or a trialkyl silyloxy group.

$R^8$ represents a hydrocarbon group. They may each be identical or different, but the preference is for them to be identical. $R^8$ is preferably an alkyl group, more preferably an alkyl group containing one to three carbon atoms and most preferably a methyl group.

This reaction is conducted in an aqueous solution or a mixed solvent of water and an organic solvent. At this point, dimethoxy ethane (DME), tetrahydrofuran (THF), acetonitrile, dioxane, alcohols containing no more than four carbon atoms and the like may be cited as the organic solvent that readily blends with water used in the mixed solvent with water. DME, THF, acetonitrile and dioxane are preferred examples. The mix ratio of an organic solvent and water is not particularly restricted, but the mixture generally contains at least 1% by weight of water and the presence of at least 5% by weight is more preferred.

The amount of the aqueous solution or mixed solvent used should be appropriately considered. Ordinarily, however, the use of the amount necessary to dissolve the starting material substances and the catalyst, for example, from two times the weight to fifty times the weight is considered.

The HCHO/silicon enolate molar ratio in a reaction solution is from 0.1 to 10, more preferably about 0.5 to 2. In addition, the catalyst is used at from 1% by mole to 50% by mole, more preferably from 5% by mole to 20% by mole in the reaction system.

The reaction temperature is ordinarily from −40° C. to ambient temperature, more preferably from −20° C. to 0° C.

The reaction time may be selected appropriately and from 0.5 hours to sixty hours, for example, is selected.

An optically active hydroxymethylated compound is formed by this reaction in excellent yield and selectivity.

The present invention is illustrated below by using the examples, but these are not intended to restrict the scope of the present invention.

Production Example 1

A ligand (henceforth referred to as "the ligand 1") having the structure shown by the formula below (chemical formula 4) was prepared according to the method described in Reference 5. The synthesis route is shown in FIG. 1.

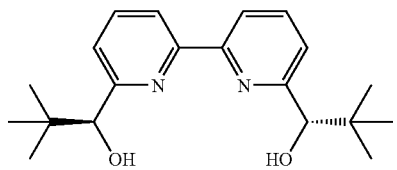

After treating 2,6-dibromopyridine (1) in ether using n-butyl lithium, compound (2) was obtained through acylation using pivalonitrile. The carbonyl group of the compound (2) was reduced stereoselectively using (−)-DIP-chloride with ee>99%. A 2,2'-bipyridine isomer (4) (R,R) (Chemical formula 4), a C2 symmetric, was obtained by conducting a homo coupling reaction of the alcohol (3) using nickel.

Production Example 2

Figure 2:
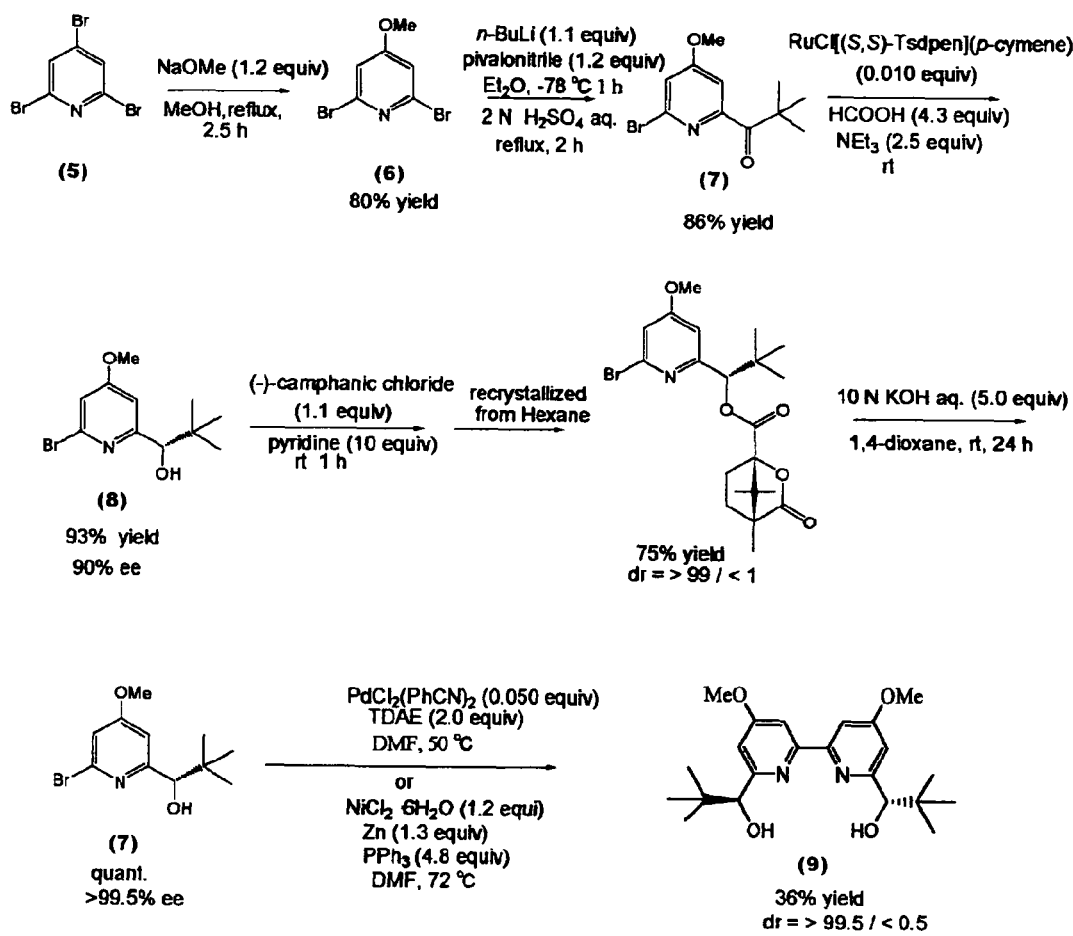
FIG. 2 shows a synthetic route for Ligand 2.

The ligand (henceforth referred to as "ligand 2") having the structure shown by the formula below (chemical formula 5) was prepared. The synthesis route is shown in FIG. 2.

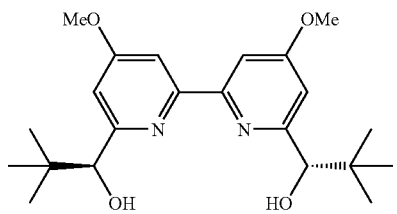

2,6-Dibromo-4-methoxy pyridine (6) was obtained in 80% yield when 2,4,6-tribromopyridine (5) was allowed to react with sodium methoxide (1.2 eq) in refluxing methanol. The compound (6) was treated using n-butyl lithium (1.2 eq.), was allowed to react with pivalonitrile (1.2 eq.) for 150 minutes at −78° C. and was refluxed for two hours in two normal sulfuric acid to yield ketone isomer (7) in 86% yield. An optically active alcohol (8) was obtained in 93% yield and in 90% ee optical purity from compound (7) through hydrogen transfer type asymmetric reduction of formic acid (4.3 eq.) and triethylamine (2.5 eq.) using the asymmetric ruthenium catalyst (RuCl[(S,S]-Tsdpen)(p-cumene), 0.01 eq.) as the catalyst. The compound (8) was converted to a camphor ester using the acid chloride, an optical resolution process was conducted using re-crystallization (75% yield, diastereomer ratio=>99/<1) and saponified again to obtain an almost optically pure alcohol (7, quant.). The compound (7) was subjected to homo coupling using a palladium catalyst [PdCl$_2$(PhCN)$_2$-TDAE] to yield a pyridine isomer (9) (Chemical formula 5) in 36% yield (diastereomer ratio=>99.5/<0.5).

Example 1

DME (0.50 ml) was added to Sc(OTf)$_3$ (0.9 mg, 0.020 mmole) that had been dried for an hour at 200° C. under vacuum. The ligand 1 (7.9 mg, 0.024 mmole) synthesized in Production Example 1 was added to this solution, and the mixture was agitated at room temperature until it became clear. The solution was cooled to −20° C., and an aqueous HCHO solution (85.8 mg, 35% w/w, 1.0 mmole) and the silicon enolate (41 mg, 0.200 mmole) derived from propiophenone, the structure of which is shown in Table 1, were subsequently added. The mixture was agitated for twenty-four hours, and a saturated aqueous sodium bicarbonate solution was subsequently added. The aqueous layer was extracted three times using CH$_2$Cl$_2$. The organic layer was dried using Na$_2$SO$_4$, the solvent was removed by distillation under reduced pressure, and the residue was purified using silica gel thin layer chromatography (hexane:AcOEt=2:1).

$^1$H NMR (CDCl$_3$) δ 1.24 (d, 3H, J=7.1 Hz), 2.35 (brs), 3.68 (ddq, 1H, J=4.3, 7.0, 7.1), 3.80 (dd, 1H, J=4.3, 11.1 Hz), 3.94 (dd, 1H, J=7.0, 11.1 Hz), 7.48 (dd, 2H, J=7.3, 8.5), 7.58 (t, 1H, J=7.3), 7.97 (d, 2H, J=8.5); $^{13}$C NMR (CDCl$_3$) δ 14.5, 42.9, 64.5, 128.4, 128.7, 133.3, 136.1, 204.4; IR (neat) 3415, 2936, 1681, 1448, 974, 704 cm$^{-1}$; MS m/z 164 (M$^+$); Anal. Calcd for C$_{10}$H$_{12}$O$_2$: C, 73.15; H, 7.37. Found: C, 72.87; H, 7.40; HPLC (Daicel Chiralpak AD-H, hexane/i-PrOH=19/1, flow rate=1.0 mL/min) R isomer: t$_R$=20.0 min, S isomer: t$_R$=17.2 min.

Example 2

The same reaction conducted in Example 1 was executed using the ligand 2 synthesized in Production Example 2 in place of the ligand 1 synthesized in Production Example 1.

Examples 3-14

The silicon enolates shown in Table 1 were allowed to undergo the same reaction described in Example 1 using the reaction time described in the same table. However, the reaction was executed at a reaction temperature of −40° C. in Example 13 and a reaction temperature of −10° C. in Example 14.

The yield and optical purity of the optically active hydroxymethylated compounds formed in Examples 1-14 are shown in Table 1. The data indicate that optically active hydroxymethylated compounds were formed in high yields.

[Table 1]

| Example | Silicone Enolates | Time (h) | Yield (%) | ee (%) |
|---|---|---|---|---|
| 1 | (OSiMe$_3$, phenyl propenyl) | 24 | 80 | 80 |
| 2[a] | | 30 | 60 | 87 |
| 3 | (OSiMe$_3$, phenyl butenyl) | 30 | 66 | 88 |
| 4 | (Me$_3$SiO, methyl indenyl) | 14 | 90 | 90 |
| 5 | (OSiMe$_3$, methyl dihydronaphthalenyl) | 20 | 80 | 94 |
| 6 | (OSiMe$_3$, cyclohexenyl) | 29 | 22 | 62[b] |
| 7 | (OSiMe$_3$, methyl cyclohexenyl) | 20 | 68 | 91[b] |
| 8 | (OSiMe$_3$, Ph cyclohexenyl) | 21 | 63 | 60 |
| 9 | (OSiMe$_3$, benzyl cyclohexenyl) | 19 | 77 | 67 |
| 10 | (Me$_3$SiO, methyl cycloheptenyl) | 2 | 62 | 90[b] |

-continued

| Example | Silicone Enolates | Time (h) | Yield (%) | ee (%) |
|---|---|---|---|---|
| 11 | 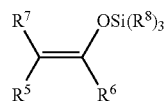 OSiMe₃ | 10 | 50 | 85[b] |
| 12[c] | OSiMe₃ / S^tBu | 24 | 31 | 93 |
| 13[d] | OSiMe₃ / Ph | 65 | 73 | 92[b] |
| 14[e] | TBSO—OSiMe₃ / Ph | 8 | 61 | 77 |

[a] Used Ligand 2.
[b] The ee was decided using chiral HPLC after converting the product into a benzoate.
[c] HCHO (ten equivalent), H₂O/DME = 1/4
[d] Reaction temperature -40° C.
[e] Reaction temperature -10° C.

POTENTIAL INDUSTRIAL APPLICABILITY

The optically active hydroxymethylated compounds formed according to the method of the present invention are useful as synthetic intermediates and the like for various chemical products.

What is claimed is:

1. A method for producing an optically active hydroxymethylated compound, comprising reacting a silicon enolate and formaldehyde, in the presence of a catalyst, in an aqueous solution or a mixed solvent of water and an organic solvent,
   wherein the silicon enolate is represented by the following formula:

$$\begin{array}{c} R^7 \quad OSi(R^8)_3 \\ \diagdown \!\!\! = \!\!\! \diagup \\ R^5 \quad R^6 \end{array}$$

wherein $R^5$ represents a hydrogen atom or an alkyl group and $R^6$ represents an alkyl group, a phenyl group, a benzyl group, a phenyl ethyl group, or a phenyl vinyl group, or
   wherein $R^5$ and $R^6$ may together with the carbon atoms to which they are bonded form an indene, 1,2-dihydronaphthylene, cyclohexene, cycloheptene or cyclopentene ring, $R^7$ represents a hydrogen atom, an alkyl group, a phenyl group, a benzyl group, a phenyl ethyl group, or a phenyl vinyl group, and the $R^8$ groups, which may be identical or different, are each alkyl groups, and
   the catalyst is obtained by mixing a ligand or its symmetric isomer and a Lewis acid,
   wherein the ligand is represented by the following formula:

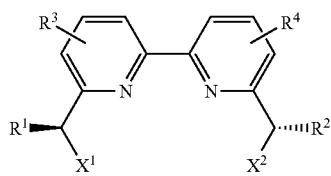

wherein each $R^1$ and $R^2$ group, which may be identical or different, is an alkyl group, provided that at least one of $R^1$ and $R^2$ contains at least three carbon atoms, the $R^3$ and $R^4$ groups, which may be identical or different, are each hydrogen atoms, alkyl groups containing one to four carbon atoms or alkoxy groups, the $X^1$ and $X^2$ groups, which may be identical or different, are each —OH or —OMe, and
   the Lewis acid is represented by $MY_n$, wherein M is Cu, Zn, Fe, Sc or a lanthanoid element, Y is a halogen atom, OAc, OCOCF₃, ClO₄, SbF₆, PF₆ or OSO₂CF₃ and n is 2 or 3.

2. A catalyst obtained by mixing a ligand or its symmetric isomer and a Lewis acid, wherein the ligand is represented by the following formula (chemical formula 1):

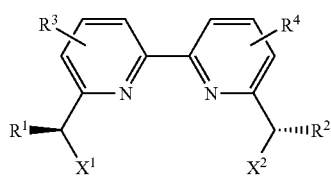

wherein each $R^1$ and $R^2$ group, which may be identical or different, is an alkyl group, provided at least one of $R^1$ and $R^2$ contains at least three carbon atoms, $R^3$ and $R^4$, which may be identical or different, are hydrogen atoms, alkyl groups containing one to four carbon atoms or alkoxy groups, and $X^1$ and $X^2$, which may be identical or different, are —OH or —OMe, and
   the Lewis acid is represented by $MY_n$, wherein M is Zn, Fe, Sc or a lanthanoid element, Y is a halogen atom, OAc, OCOCF₃, ClO₄, SbF₆, PF₆ or OSO₂CF₃ and n is 2 or 3.

* * * * *